United States Patent
Beverly et al.

(10) Patent No.: US 6,632,855 B1
(45) Date of Patent: Oct. 14, 2003

(54) BIOCIDAL PLASTIC MATERIAL

(75) Inventors: Gordon Maxwell Beverly, Lancashire (GB); Michael John Ellacott, Lancashire (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 09/646,044

(22) PCT Filed: Mar. 16, 1999

(86) PCT No.: PCT/GB99/00686

§ 371 (c)(1),
(2), (4) Date: Jan. 3, 2001

(87) PCT Pub. No.: WO99/47595

PCT Pub. Date: Sep. 23, 1999

(30) Foreign Application Priority Data

Mar. 17, 1998 (GB) .............................................. 9805487

(51) Int. Cl.$^7$ .............................. C08K 3/10; C08K 3/22
(52) U.S. Cl. ........................ 523/122; 523/201; 523/351; 525/902; 428/521
(58) Field of Search ................. 523/122, 351, 523/201; 525/902; 428/521; 524/403

(56) References Cited

U.S. PATENT DOCUMENTS

| | | | | |
|---|---|---|---|---|
| 3,636,138 A | * | 1/1972 | Beer ........................... | 525/902 |
| 4,008,351 A | | 2/1977 | Inoue et al. | |
| 4,468,487 A | * | 8/1984 | Schepers et al. ............ | 524/100 |
| 4,677,003 A | * | 6/1987 | Redlich et al. .............. | 525/902 |
| 4,983,648 A | * | 1/1991 | Laughner et al. ............ | 523/351 |
| 5,096,948 A | * | 3/1992 | Kurumada et al. .......... | 524/102 |
| 5,304,707 A | * | 4/1994 | Blankenship et al. ........ | 523/201 |
| 5,486,407 A | * | 1/1996 | Noell et al. ............. | 156/244.11 |
| 5,614,568 A | * | 3/1997 | Matawari et al. ............ | 523/122 |
| 5,698,229 A | * | 12/1997 | Ohsumi et al. .............. | 523/122 |

FOREIGN PATENT DOCUMENTS

| | | | |
|---|---|---|---|
| EP | 0606762 | | 7/1994 |
| JP | 5331345 | * | 12/1993 |
| JP | 294007 | * | 4/1994 |
| JP | 76286 | * | 9/1994 |
| JP | 6263956 | * | 9/1994 |
| JP | 107610 | * | 10/1994 |
| JP | 6287403 | * | 10/1994 |
| JP | 124825 | * | 11/1994 |
| JP | 7053832 | * | 2/1995 |
| JP | 311086 | * | 6/1996 |

OTHER PUBLICATIONS

Database WPI, Section Ch, Week 9504, Derwent Publications, London, GB; AN 95–027690.

* cited by examiner

*Primary Examiner*—Peter Szekely
(74) *Attorney, Agent, or Firm*—Pillsbury Winthrop LLP

(57) ABSTRACT

A plastics material comprises an acrylic polymer containing 5–50% of a rubbery copolymer and a biocidal compound. The plastic material is useful as a component of a refrigerator, worktop etc. or as a building material. The material may be used as a coating for a substrate. Method of manufacturing laminate materials comprising the plastics material are also claimed.

25 Claims, No Drawings

BIOCIDAL PLASTIC MATERIAL

The present invention relates to plastics materials, in particular to plastics which are resistant to the growth of certain microbiological species, such as fungi or bacteria.

Plastics materials are very commonly used in the manufacture of a wide variety of articles such as refrigerators, worktops, shelves etc. These articles may be likely to come into contact with biological species which are harmful to health and which may spread and grow upon the surface of the article. The control of harmful microbes is also desirable in certain medical applications when the growth of bacteria etc. on benchtops, trays etc. is to be prevented. The incorporation of a biocidal compound into the plastics used in such applications may therefore provide beneficial effects in that the growth of bacteria or fungi on the lining of a fridge, for example, may be inhibited.

Certain polymeric materials, e.g. polyvinylchloride, are susceptible to biological attack, especially from fungi. In order to reduce or prevent the degradation of plastics resulting from such biological attack, biocidal products have been developed for incorporation into plastics materials or paints to kill the fungi or bacteria responsible or prevent their proliferation. It is also known to incorporate biocidal compounds into plastics to prevent the growth of bacteria or fungi found in food products. Examples of the latter type of product are described in U.S. Pat. No. 5,433,424, JP-A-06287403 and JP-A-07071 869 amongst others, and articles such as food-praparation surfaces and household food containers etc are already widely available to consumers.

WO-96/29361 describes a biocidal polymeric matrix comprising a support matrix, an antimicrobial agent and a carrying agent, wherein the carrying agent and the antimicrobial agent are adapted to form at least one hydrogen bond or salt bridge therebetween.

WO 96135205 describes a white cover for piano keys formed by injection moulding a homogeneous dispersion of a methyl methacrylate resin and 0.5–2% of an antibacterial agent comprising a ceramic body prepared by sintering and mixing calcium phosphate and metallic silver.

WO 98/21253 describes polymers which have antimicrobial properties consisting of copolymers of non-functional vinyl monomers with vinyl comonomers of specified composition having ionic functionality.

WO 96/22023 describes the use of 2-alkyl or 2-aralkyl benzisothiazolin-3-one derivatives as fungicides for plastics materials.

JP-A-08257493 describes the use of a steel plate which has a paint coating incorporating inorganic aggregates containing anti-bacterial compound, as a lining for refrigerators, freezers or heating cabinets.

JP-A-08145394 and JP-A08145392 describe the use of plastics incorporating anti-microbial compounds for use in ventilator apparatus.

EP-A-606762 describes a composition of a styrene polymer, an antibacterial agent and a compound having a specific functional group to produce an antibacterial resin composition.

U.S. Pat. No. 4,533,435 describes an antimicrobial paper for packaging surgical supplies which incorporates antibacterial compounds in a vinylic polymer binding agent.

The incorporation of antimicrobial agents is reviewed by D. Smock in Plastics Formulating and Compounding, March/April 1997 page 16 and Plastics World March 1992 page 58.

The present invention provides a plastics material which has biocidal activity which is useful in the manufacture of articles having biocidal properties e.g. for use in food storage and preparation areas or medical applications. By "biocidal" we include biostatic activity, i.e. where the proliferation of microbiological species is reduced or eliminated in addition to true biocidal activity where microbiological species are killed. We also include activity against fungi, bacteria and other microbiological species in the meaning of "biocidal".

According to the invention, we provide a plastics material having biocidal activity comprising an acrylic polymeric material and a biocidal compound wherein said acrylic material incorporates from 5% to 50% by weight of the total polymer present of a rubbery copolymer.

Preferred biocidal compounds include triclosan, compounds based on heavy metals, especially silver, on inorganic carriers such as zeolites, hydroxyapatite, zinc oxide, titanium dioxide, zirconium phosphate, isothiazolones, benzisothiazolin-3-one derivatives, 10, 10' oxybisphenoxy-arsine, isothiazolines, zinc pyrithione, folpet (trichloromethyl thio-phthalimide). Examples of biocidal compounds which are effective in the invention include those sold under the trademarks DENSIL™ S (2,3,5,6 tetrachloro-4(methyl sulphonyl)pyridine available from Zeneca Ltd), SK-NOB-Z™ (a silver-containing zirconium phosphate available from Sanai of Japan) and VANQUISH™ (n-butyl 1,2-benzisothiazoline available from Zeneca Ltd). The present invention is directed towards improving the biocidal activity of acrylic materials containing known biocidal compounds and not to the biocidal compounds themselves and so it is envisaged that biocidal compounds other than those listed above may also be effectively used in the acrylic materials of the invention. The selection of any particular biocide for articles of the invention must be made with due regard to the end-use of the article and to the particular properties of the biocide, i.e. its activity against certain types of micro-organisms, toxicity, processability etc. It is not within the teaching of this document to provide guidance on the suitability of any one biocidal compound for any particular end-use.

The biocide is preferably present at a concentration of at least 0.25% by weight, more preferably at least 1% by weight of the polymer, e.g. 0.5–3% by weight.

The acrylic polymeric material comprises a homopolymer or copolymer of at least one $C_{1-6}$ alkyl ($C_{0-8}$alk)acrylate. Preferred acrylic materials are homopolymers or copolymers of the methyl, ethyl, butyl, 2-ethylhexyl, cyclohexyl or phenyl esters of acrylic acid or methacrylic acid. One example of a preferred acrylic material comprises a homopolymer or copolymer of methyl methacrylate a copolymer comprising 80–100% of methyl methacrylate residues and 0–20% of a comonomer of a further acrylate or methacrylate selected from those materials listed above.

The composition of the acrylic material is selected according to the application in which the material is to be used. For example, if the plastics material is intended to be extruded into a sheet for subsequent thermoforming, e.g. to form a lining for a refrigerated cabinet, then an acrylic material formulated for thermal moulding should be selected. Such acrylic materials may advantageously be copolymers of methyl methacrylate with a minor amount (e.g. 1–20 % wt) of an alkyl acrylate, e.g. methyl, ethyl or butyl acrylate and having a molecular weight of less than 500,000. For example a suitable copolymer is derived from about 90% methyl methacrylate and about 10% of ethyl acrylate having a weight average molecular weight of about 80,000–120,000. The acrylic plastics material may be used as a coating over a base material which may be another polymer, such as another acrylic layer, PVC or a styrene based polymer for example. Acrylic materials have good weathering and chemical resistance as well as providing a high gloss finish and therefore a coating of acrylic having these properties may be provided to impart a suitable surface finish to another article. The acrylic polymer may contain additives such as fillers, colorants, impact modifiers, matting agents etc.

The acrylic material incorporates from 5% to 50% by weight of the total polymer present of a rubbery copolymer. By a rubbery copolymer, we mean materials which have a glass transition temperature which is less than room temperature, preferably less than 0° C., e.g. less than –20° C. We also incide block copolymers which include a rubbery, low $T_g$ block, often with harder, higher $T_g$ blocks. Such materials are well known for use as toughening agents for improving the impact resistance of acrylic materials. Suitable rubbery copolymers include copolymers of acrylates, methacrylates, styrene, acrylonitrile and/or olefins (especially butadiene). Examples of suitable materials include styrene—butadiene rubbers, such as the Cariflex™ polymers supplied by Shell, styrene-olefin copolymers such as styrene ethylene-butylene styrene (optionally containing succinic anhydride), styrene-ethylene propylene, e.g. the polymers sold under the Kraton trademark by Shell, methacrylate-butadiene-styrene (MBS) terpolymers, styrene-acrylonitrile copolymers, e.g. acrylonitrile-butadiene-styrene (ABS) terpolymers and core-shell type particles based on alkyl acrylates, e.g. butyl acrylate and styrene. Preferred types of rubbery copolymer include copolymers of styrene, butadiene and a methacrylate compound, e.g. MBS copolymers. We have found that the incorporation of such rubbery materials enhances the biocidal effect of biocidal compounds incorporated into the acrylic materials. Preferably the plastics material comprises 15–50% by weight of rubbery polymer, especially 20–45%.

Suitable core-shell particles are discrete particles made by multi-stage graft copolymerisation normally by emulsion polymerisation techniques, each having a multi-layer structure and generally used to improve the impact resistance of polymers such as acrylic materials. A wide variety of these particles is available which differ in the type of copolymers from which they are made and the number and volume of shells present around the core. Typically the core is made from a methacrylate homo or copolymer and the first shell provides the rubbery material having a low $T_g$, typically made from an alkyl acrylate/styrene copolymer. This shell is often formulated to provide a rubbery character for impact modification whilst being matched in refractive index to the acrylic substrate into which it is to be incorporated. A preferred type of copolymer to form the shell is based on n-butyl acrylate and an aromatic comonomer, e.g. styrene or a derivative thereof. A second or subsequent shell may also be present. Many suitable core-shell paricles are commercially available, e.g. IR441 available form Mitsubishi Rayon Co., and some commercially available grades of acrylic moulding materials include similar materials pre-compounded in to the polymer. One suitable core-shell particle is described in WO96/37531 and comprises a (meth) acrylic polymer core, a first shell comprising a low Tg polymer comprising 0–25% by weight of a styrenic monomer and 75–100% of an acrylic monomer, the (meth)acrylic monomer being capable of forming a homopolymer having a Tg in the range –75 to –5° C., the first shell representing at least 65% by volume of the combined volume of the core and first shell, and optionally a second shell which comprises a second (meth)acrylic polymer which may be the same as or different from the first (meth)acrylic polymer and the core and first shell together contain from 0.5–1.0% by weight of a graft cross-linker.

The plastics material of the invention may have many applications. It is useful as a resin for moulding or extrusion applications, e.g. to make doors or panels for interior or exterior cladding applications etc. It may be provided in the form of a sheet material, e.g. for providing walls, linings etc or which may be suitable for forming into articles such as bathtubs e.g. by thermoforming. It may also be useful in the form of a curable resin, e.g. a polymethyl methacrylate resin dissolved in methyl methacrylate and optionally containing a dispersion of fillers, colours and other functional particles for the manufacture of sinks, worktops, shower trays etc. The plastics material of the invention may be especially useful as a coating on a substrate. One benefit of this form of the invention is that a relatively small amount of the biocidally active plastic may be used to give biocidal function to the surface of a non-biocidal substrate.

In a second aspect of the invention therefore, we provide a laminate material comprising a substrate material in contact with a layer of a plastics material having biocidal activity comprising an acrylic polymeric material and a biocidal compound wherein said acrylic material incorporates from 5% to 50% by weight of the total polymer present of a rubbery copolymer. The thickness of the biocidal layer relative to the substrate may vary widely e.g. from 100% (i.e. equal thickness) to less than 1%. Normally the biocidal layer would be relatively thin, e.g. less than 50%, preferably less than 20% of the thickness of the substrate. One particular benefit of providing the plastics material having biocidal activity as a relatively thin layer on top of a transparent substrate, e.g. transparent acrylic material, is that when the biocidal layer is sufficiently thin, a substantially transparent or translucent laminate material may be produced. This type of material is useful for producing articles in which a transparent or translucent effect is desired in combination with biocidal activity at the surface of the material. Such applications include material from which internal fittings for refrigerators are made, shelving for food products, shower screens etc.

The substrate material preferably comprises a thermoplastic material selected from the group comprising polystyrene and copolymers of styrene, acrylic polymers and copolymers, polyvinyl chloride and polyolefins and copolymers of these materials, e.g. acrylonitrile-styrene-butadiene (ABS). The substrate may contain additives such as fillers, pigments, plasticisers, impact modifiers, stabilisers etc. The biocidal layer may be applied to the substrate by coextrusion, extrusion coating, or adhesive or heat-and-pressure lamination of a sheet or film of the biocidal plastics material to the substrate material.

Of particular interest for the production of transparent materials is the use of core-shell impact modifier particles as the rubbery copolymer in the biocidal acrylic material or layer. This is because such core-shell particles may be formulated to have a refractive index which is matched to that of the acrylic material and therefore they may be incorporated into transparent grades of acrylic without reducing significantly the transparency of the acrylic material. Therefore it is possible to improve the biocidal effect of biocides incorporated into acrylic materials by incorporating a core-shell impact modifier which has been selected to match the refractive index of the acrylic material. When an acrylic material incorporating a core-shell particle and a biocide is provided as a thin (e.g. less than 200 µm) layer on a thicker transparent layer of acrylic material then the benefits of biocidal activity may be provided whilst retaining the transparency of the acrylic.

In a further aspect of the invention we provide a method of manufacturing a laminate material comprising the steps of extruding a plastics material having biocidal activity comprising an acrylic polymeric material and a biocidal compound wherein said acrylic material incorporates from 5% to 50% by weight of the total polymer present of a rubbery copolymer on top of a layer of a substrate material. The substrate material preferably comprises a thermoplastic material which is coextruded with said plastics material having biocidal activity.

The invention will be further described with reference to the following examples.

EXAMPLE 1

Comparative

An acrylic plaque was made by compounding together in a twin-screw extruder at 200–220° C. an injection moulding grade of acrylic polymer (Diakon™ LG156 from ICI Acrylics) with 2% of Vanquish™ 100 biocide from Zeneca Specialties. The biocide was added to the polymer melt by means of a liquid injection system and the resulting mixture was formed into a lace which was cut into small chips. A 50 mm (2")×75 mm (3")×3 mm test plaque was formed by injection moulding at 220° C. into a mould pre-heated to 40° C. The sample plaque was then tested for fungal resistance and bacterial growth as described below. The results are given in Table 1.

Fungal Resistance

The samples were tested according to ASTM G21-90. Two 25 mm squares were cut from each sample and placed onto minimal salts agar plates. The plates were inoculated with a mixed fungal suspension containing aspergillus niger, aureobasidium pullulans, chaetomium globosum, gliocladium virens, penicillium funiculosum and then incubated for 28 days at 20° C. The samples were then examined for fungal growth and rated as follows: NG (no growth), TG (trace growth) <10% coverage on test piece, LG (light growth)—10–30% coverage, MG (moderate growth) 30–60% coverage, HG (heavy growth) 60% to complete coverage.

Bacterial Growth

EXAMPLES 1–10

0.2 ml of a 24 hour suspension of *Escherichia coli* was placed onto the surface of a test piece cut from a sample and then covered with a microscope coverslip. The samples were incubated for 24 hours at 30° C. and then rinsed with 10 ml of sterile saline solution. The bacteria in the rinse water were then counted using a serial dilution counting method in nutrient agar. The control sample was run with the *E. coli* suspension placed directly onto a sterile petri dish and covered with a coverslip.

EXAMPLES 2–5

Plaques of acrylic material were made and tested as described in Example 1, but with the addition of MBS (KANE™ ACE 56, available from Kaneka) at varying levels at the compounding stage. The results are given in Table 1.

EXAMPLES 6–9

Sample plaques containing 35% by weight of MBS and varying levels of Vanquish 100 biocide were made and tested according to the method described above. The results are given in Table 1.

EXAMPLE 10

A sample plaque containing 35% MBS and 2% Densil™ S biocide from Zeneca Specialties was made and tested by the method described above. The results are given in Table 1.

TABLE 1

| Example | Wt % MBS | Wt % biocide | Bacterial count | Fungal growth rating |
|---|---|---|---|---|
| 1 | 0 | 2.00 | $2.5 \times 10^3$ | HG/HG |
| 2 | 15 | 2.00 | $4.3 \times 10^3$ | HG/HG |
| 3 | 25 | 2.00 | $3.4 \times 10^2$ | HG/HG |
| 4 | 35 | 2.00 | $0 \times 10^1$ | NG/NG |
| 5 | 45 | 2.00 | $0 \times 10^1$ | NG/NG |
| 6 | 35 | 1.00 | $3.0 \times 10^3$ | MG/MG |
| 7 | 35 | 0.5 | $9.0 \times 10^3$ | HG/HG |
| 8 | 35 | 0.25 | $3.2 \times 10^4$ | HG/HG |
| 9 | 35 | 0.00 | $6.0 \times 10^5$ | HG/HG |
| 10 | 35 | 2.00 | $6.3 \times 10^2$ | LG/MG |

EXAMPLE 11

Layered Sample by Coextrusion

A mixture containing 63 wt % Diakon™ LG156, 35% MBS polymer and 2% Vanquish™ 100 antibacterial compound was compounded together and formed into polymer chips as described in Example 1. The resulting acrylic polymer was then coextruded at a thickness of 50–100 $\mu$m onto a a 1 mm thick clear acrylic layer formed from unmodified Diakon™ LG156. The sample appeared translucent. The bacterial growth tests were performed, as described below, on the side of the sample containing biocidal compound. The results are shown in Table 2. The ASTM G21-90 Fungal resistance test gave a result of "no growth".

Bacterial Growth Tests

EXAMPLES 11–16

The samples were tested by a modified tile test vs *Escherichia coli* NCTC 8196. Sections of acrylic (50 mm×50 mm) were wiped with isopropyl alcohol and then placed in petri dishes. The surface of the acrylic sample was inoculated with 0.1 ml of a culture of the organism in ¼ strength Ringers solution. The acrylic was then covered with a sterilised glass slide. The samples were maintained at 20° C. +/−1° C. at >90% RH for 72 hours. The surviving organisms were recovered by washing/swabbing the acrylic and glass surfaces with 10 ml of Tryptone soya broth containing inactivators. Recoveries were performed at 24, 48 and 72 hours. The resulting broth was serially diluted and plate counts using plate count agar containing inactivators were performed. Plates were incubated at 37° C. for 48 hours. Glass slides were used for control counts.

EXAMPLE 12

Comparative

A comparative sample containing 2% Vanquish and 98% LG156 was made as described in Example 11 and tested. The ASTM G21-90 Fungal resistance test gave a result of "moderate growth"

EXAMPLE 13

Comparative

A comparative sample was made by coextruding unmodified LG156 onto unmodified LG156 substrate as described in Example 11. The ASTM G21-90 Fungal resistance test gave a result of "moderate growth".

EXAMPLE 14

A mixture containing 63 wt % Diakon™ LG156, 35% MBS polymer and 2% Irgasan™ DP300 (triclosan supplied by Ciba Speciality Chemicals) antibacterial compound was compounded together and formed into polymer chips and then coextruded and tested as described in Example 11.

EXAMPLE 15

Comparative

A sample containing 2% tridosan and 98% LG156 was made and tested. The results are shown in Table 2.

EXAMPLE 16

A mixture containing 63 wt % Diakon™ LG156, 35% of a core-shell impact modifier based on MMA/butyl acrylate/styrene copolymers and made as described in the example of WO 96/37531, and 2% Vanquish™ 100 antibacterial compound was compounded together and formed into polymer chips and then coextruded and tested as described in Example 11. The coextruded sample was clear—transparent and very slightly yellow.

EXAMPLE 17

A mixture containing 63 wt % Diakon™ LG156, 35% of IR441™ which is a core-shell impact modifier (Mitsubishi Rayon Co). and 2% Vanquish™ 100 antibacterial compound was compounded together and formed into polymer chips and then coextruded and tested as described in Example 11. The coextruded sample was dear—transparent and very slightly yellow.

The samples were tested again for bacterial growth at 35° C. and the results are shown in Table 3.

EXAMPLE 18

The biocide+acrylic+MBS compound made in Example 11 was re-compounded and then coextruded onto a clear acrylic substrate. The biocidal growth results were very similar to those of Example 11, showing that the material can withstand two extrusion operations, whilst maintaining its biocidal activity.

TABLE 2

| Example | Rubber | Wt % rubber | Biocide | Wt % biocide | $\log_{10}$ E. coli count @ 20° C. 0 hours | 24 hours | 48 hours | 72 hours |
| --- | --- | --- | --- | --- | --- | --- | --- | --- |
| glass control | — | — | — | — | 5.3 | 5.72 | 6.82 | 6.93 |
| 11 | MBS | 35 | Vanquish | 2 | 5.3 | 1.70 | <1 | <1 |
| 12 (comp) | — | — | Vanquish | 2 | 5.3 | 5.28 | 5.40 | 4.95 |
| 13 (comp) | — | — | — | — | 5.3 | 5.32 | 5.48 | 4.92 |
| 14 | MBS | 35 | triclosan | 2 | 5.3 | 4.49 | 2.54 | 1.90 |
| 15 (comp) | — | — | triclosan | 2 | 5.3 | 4.30 | 4.18 | 4.30 |
| 16* | core-shell | 35 | Vanquish | 2 | 6.38 | 4.77 | 3.91 | 1.9 |
| 17* | IR441 core-shell | 35 | Vanquish | 2 | 6.38 | 4.85 | 2.92 | <1 |

*samples 16 and 17 were tested at a different time using a bacterial sample having a different initial count.

TABLE 3

| Example | Rubber | Wt % rubber | Biocide | Wt % biocide | $\log_{10}$ E. coli count @ 35° C. 0 hours | 24 hours | 48 hours | 72 hours |
| --- | --- | --- | --- | --- | --- | --- | --- | --- |
| glass control | — | — | — | — | 6.00 | 7.48 | 7.70 | 8.00 |
| 11 | MBS | 35 | Vanquish | 2 | 6.00 | 1.00 | — | — |
| 12 (comp) | — | — | Vanquish | 2 | 6.00 | 5.78 | 5.95 | 6.00 |
| 13 (comp) | — | — | — | — | 6.00 | 4.90 | 5.00 | 5.48 |
| 14* | MBS | 35 | triclosan | 2 | 5.30 | 1.00 | — | — |
| 15 (comp)* | — | — | triclosan | 2 | 5.30 | 3.77 | — | — |
| 16 | core-shell | 35 | Vanquish | 2 | 6.00 | 3.78 | 3.95 | 2.48 |
| 17 | IR441 core-shell | 35 | Vanquish | 2 | 6.00 | 4.60 | 4.30 | 3.90 |

*samples 14 and 15 were tested at a different time using a bacterial sample having a different initial count.

What is claimed is:

1. A plastics material having biocidal activity comprising a melt compounded acrylic polymeric material comprising a homopolymer of a $C_{1-6}$alkyl($C_{0-8}$alk)acrylate or a copolymer of methyl methacrylate and up to 20% of a comonomer of a $C_{1-6}$alkyl($C_{0-8}$alk)acrylate, and a biocidal compound wherein said acrylic material incorporates from 5% to 50% by weight of the total polymer present of a rubbery copolymer.

2. A plastics material as claimed in claim 1, wherein said acrylic material incorporates from 25% to 50% by weight of the total polymer present of a rubbery copolymer.

3. A plastics material as claimed in claim 1, wherein said biocidal compound is selected from the group consisting of: triclosan, heavy metal compounds on inorganic carriers, isothiazolones, benzisothiazolin-3-ones, 10, 10' oxybisphenoxyarsine, isothiazolines, zinc pyrithione, folpet (trichloromethylthio-phthalimide), and 2,3,5,6 tetrachloro-4 (methyl sulphonyl)pyridine.

4. A plastics material as claimed in claim 1, wherein said biocidal compound comprises at least 0.25% by weight of the plastics material.

5. A plastics material as claimed claim 1, which is in the form of a thermoformable sheet.

6. A plastics material as claimed in claim 1 which is in the form of a surface coating layer supported on a substrate material.

7. A plastics material as claimed in claim 1 which is in the form of a curable resin composition.

8. A plastics material as claimed in claim 1 which is in the form of a moulding resin or moulded article.

9. A plastics material as claimed in claim 1, wherein the rubbery material comprises a copolymers of an alkyl acrylate with styrene and optionally other copolymers.

10. A plastics material as claimed in claim 9, wherein the rubbery material is in the form of a core-shell particle.

11. A laminate material comprising a substrate material in contact with a layer of a plastics material having biocidal activity comprising a melt compounded acrylic polymeric material comprising a homopolymer of a $C_{1-6}$alkyl($C_{0-8}$alk) acrylate or a copolymer of methyl methacrylate and up to 20% of a comonomer of a $C_{1-6}$alkyl($C_{0-8}$alk)acrylate, and a biocidal compound wherein said acrylic material incorporates from 5% to 50% by weight of the total polymer present of a rubbery copolymer.

12. A laminate material as claimed in claim 11, wherein said substrate material comprises a thermoplastic material selected from the group comprising polystyrene and copolymers of styrene, acrylic polymers and copolymers, polyvinyl chloride and polyolefins.

13. A method of manufacturing a laminate material comprising extruding a plastics material having biocidal activity comprising a melt compounded acrylic polymeric material comprising a homopolymer of a $C_{1-6}$alkyl($C_{0-8}$alk)acrylate or a copolymer of methyl methacrylate and up to 20% of a comonomer of a $C_{1-6}$alkyl($C_{0-8}$alk)acrylate, and a biocidal compound wherein said acrylic material incorporates from 5% to 50% by weight of the total polymer present of a rubbery copolymer.

14. A method as claimed in claim 13, wherein said substrate material comprises a thermoplastic material which is coextruded with said plastics material having biocidal activity.

15. A refrigerator part comprising a plastics material or a laminate material as claimed in claim 1.

16. A refrigerator part as claimed in claim 15, in the form of a lining, door panel, shelf or storage box.

17. A building component comprising a plastics material or a laminate material as claim 1.

18. A plastic composition having biocidal activity consisting essentially of a melt compounded acrylic polymeric material comprising a homopolymer of a $C_{1-6}$alkyl($C_{0-8}$alk) acrylate, or a copolymer of methyl methacrylate and up to 20% of a comonomer of a $C_{1-6}$alkyl($C_{0-8}$alk)acrylate, a biocidal compound and a rubbery copolymer, wherein said rubbery copolymer is present in an amount from 5% to 50% based on the total weight of polymeric components.

19. A plastics material as claimed in claim 3, wherein said biocidal material comprises heavy metal compound on zeolite, hydroxyapatite, zinc oxide, titanium oxide or zirconium phosphate.

20. A plastics material as claimed in claim 19, wherein said heavy metal compound is a silver compound.

21. A plastics material as claimed in claim 1, wherein the acrylic polymeric material is said homopolymer.

22. A plastics material as claimed in claim 1, wherein the acrylic polymeric material is poly(methylmethacrylate).

23. A plastics material as claimed in claim 1, wherein the acrylic polymeric material is said copolymer.

24. A laminate material as claimed in claim 11, wherein the acrylic polymeric material is poly(methylmethacrylate).

25. A laminate material as claimed in claim 11, wherein the acrylic polymeric material is said copolymer.

* * * * *